United States Patent [19]

Niznick

[11] Patent Number: 5,030,095
[45] Date of Patent: Jul. 9, 1991

[54] ANGLED ABUTMENT FOR ENDOSSEOUS IMPLANTS

[76] Inventor: Gerald A. Niznick, 18161 Chardon Cir., Encino, Calif. 91316

[21] Appl. No.: 394,830

[22] Filed: Aug. 16, 1989

[51] Int. Cl.$^5$ .............................................. A61C 8/00
[52] U.S. Cl. ....................................... 433/173; 433/174
[58] Field of Search ................ 433/173, 174, 175, 176

[56] References Cited

U.S. PATENT DOCUMENTS

| | | | |
|---|---|---|---|
| 4,738,623 | 4/1988 | Driskell | 433/173 |
| 4,744,756 | 5/1988 | Ross | 433/173 |
| 4,758,161 | 7/1988 | Niznick | 433/173 |
| 4,832,601 | 5/1989 | Linden | 433/173 |
| 4,854,872 | 8/1989 | Detsch | 433/174 |

*Primary Examiner*—Cary E. Stone

[57] ABSTRACT

An angled abutment adapted for use with an endosseous dental implant includes two parts, a first part having a platform joined to a downwardly-projecting post with screw threads on its outer surface adapted for engagement in an internally-threaded shaft at the top of an endosseous dental implant, and a second part that includes an angled head joined to a shaft that projects downwardly from the head and is adapted for insertion and for cementing into the downwardly-projecting passage in the platform of the first part.

8 Claims, 6 Drawing Sheets

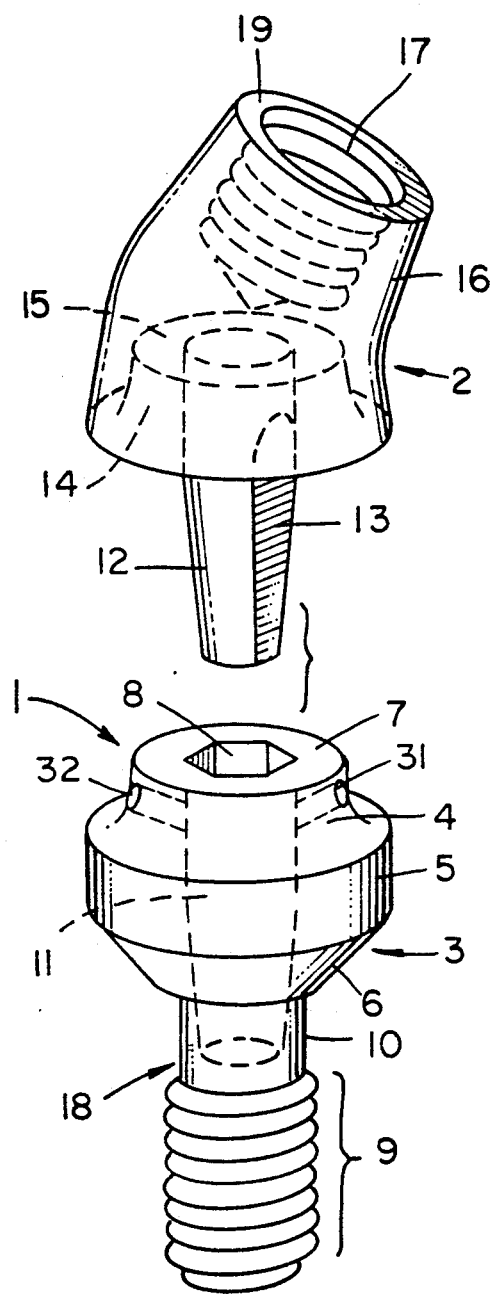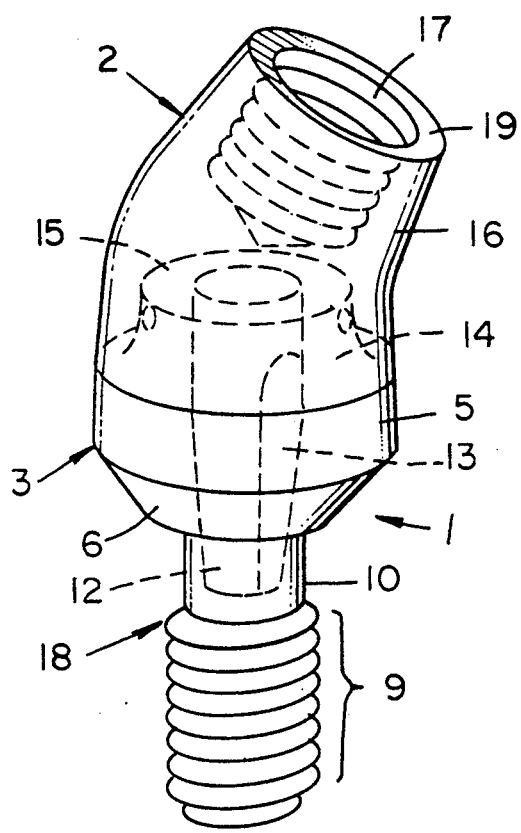
FIG. 1
FIG. 2

ANGLED ABUTMENT FOR ENDOSSEOUS IMPLANTS

This invention relates to angled abutments, sometimes called heads, adapted for use with an endosseous dental implant anchoring means. These abutments comprise two separate parts. The first part includes platform means joined to downwardly-projecting post means having screw threads on the outer surface of the post means. The threaded post means are adapted for engagement in an internally-threaded shaft at the top of an endosseous dental implant anchoring means such as the Core-Vent ® endosseous dental implant anchoring means, the Screw-Vent ® endosseous dental implant anchoring means, the Micro-Vent ® endosseous dental implant anchoring means and the Bio-Vent ® endosseous dental implant anchoring means. See FIGS. 5–8 for drawings of these implants. There, the letters A, B, C and D identify the internally-threaded shafts adapted to receive the threaded post on the first part of this new angled abutment.

The second part of the new angled abutment comprises angled head means joined to shaft means that projects downwardly from the angled head means. The downwardly-projecting shaft means is adapted for insertion and for cementing into a downwardly-projecting passage in the platform means.

In preferred embodiments, the first part of this new angled abutment means comprises a platform means having a flat upper surface with an opening in that surface leading to a downwardly-projecting shaft-receiving passage. Preferably, the opening and the passage have six flat sides, all of substantially the same length and width. The passage below the opening has a shape and size adapted to receive downwardly-projecting shaft means from the second part of the abutment means. When cemented into this passage, the downwardly-projecting shaft resists rotation in the passage, especially when the abutment is subjected to off-center occlusal forces. To this end, the downwardly-projecting shaft preferably includes at least one flat side, but otherwise has a rounded surface. In preferred embodiments, the passage is sufficiently large to permit excess cement in the passage to escape after insertion of the shaft into the passage. Where the opening passage is six-sided, for example, intersections of these sides are preferably spaced sufficiently far from the shaft of the second part to permit cement to escape from the passage. In general, when the shaft means is cemented into the passage in the platform means, the shaft resists rotational displacement and provides sufficient strength to withstand off-center occlusal forces imposed on prostheses attached to the head means of the second part of the abutment.

Projecting downwardly from the platform means is post means having external threads for engagement with an internally-threaded passage at the top of an endosseous dental implant anchoring means such as those depicted in FIGS. 5–8, respectively. The number, pitch and width of these screw threads can vary depending upon the length and dimensions of the passage adapted to receive this post means in the dental implant anchoring means.

The platform means can have any desired shape and size, but preferably has a bottom portion that is complementary to the structure at the top of the internal passage in a dental implant. More preferably, this bottom portion of the platform means is adapted to seat firmly in such structure and to seal sufficiently tightly to minimize inflow of any solid or liquid substance into such an internal passage. Above this bottom portion, the platform means preferably comprises a cylindrically-shaped portion that is adapted to sealingly engage the bottom surface of the head means in the second part of the angled abutment. In preferred embodiments, the upper portion of the platform means is frustoconical-shaped, and is complementary in size and shape to a frustoconical-shaped recess at the bottom of the head means in the second part of this abutment.

In preferred embodiments, the angled head means in the second part is joined to a downwardly-projecting shaft whose size and shape are adapted to fit within, and, before cementing, rotate freely in the passage in the platform means of the first part. The angle and direction of this head means can be varied depending upon the end use of the abutment, such as the kind of prostheses that the abutment supports, and the location of the abutment in a patient's mouth. The angled head means and the shaft means must be of sufficient size and shape to withstand occlusal forces imposed on the prostheses joined thereto.

The head means can have a tapered shape to accept a cemented prosthesis, or can have a threaded passage in its upper surface to accept a fixation screw for a detachable prosthesis. Both the tapered head and the head adapted to receive a fixation screw can be sufficiently short to support dental prostheses without compromising strength or the attachment between the two parts of the abutment.

For the head means adapted to accept a threaded upper member, the threaded member can be adapted for placement over the axis of the implant to reduce off-center occlusal forces, and to permit manufacture of aesthetic, functionally detachable restorations.

The preferred embodiments of the second part also include, at the bottom surface, a frustoconical-shaped recess. In these embodiments, the shaft means is attached to a planar surface at the bottom of this recess, and projects downwardly through the recess and below the body portion. This recess is preferably of a size and shape that is complementary to the upper end of the first part so that, when the second part is combined with the first part, the recess at the bottom of the head means sealingly engages the complementary structure of the platform means. Such sealing engagement is preferably sufficient to prevent inflow of solids or liquids into the passage in the platform means of the first part.

In preferred embodiments, the first part and the second part of the angled abutment are made of titanium or a Ti/6A1/4V alloy. Both the first and second parts are preferably made by a machining process.

The new angled abutment can better be understood by reference to the drawings in which:

FIG. 1 provides a perspective view of a preferred embodiment of the new angled abutment with the two parts separated from one another;

FIG. 2 shows the embodiment of FIG. 1 with the two parts joined together;

Figure 3:
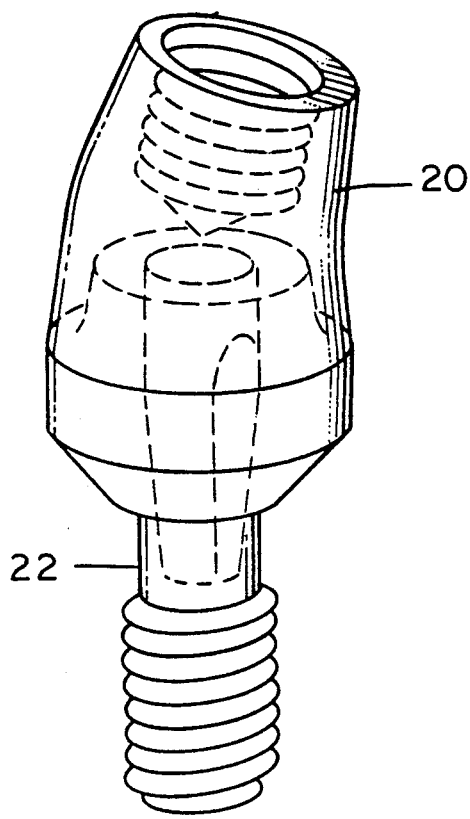
FIG. 3 shows a second embodiment of the angled abutment shown in FIG. 1.

FIG. 1 shows that first part 1 of the angled abutment includes platform means 3 joined to post means 18. Post means 18 and the hex-hole opening 8 and passage 11 to which hex-hole opening 8 leads are all on the same longitudinal axis of first part 1. Platform means 3 includes cylindrical portion 5 atop frustoconical portion 6 and below frustoconical portion 4. Above frustoconical portion 4 is flat surface 7 having hex-hole opening 8 formed therein. Post means 18 includes an unthreaded, cylindrical portion 10 and threaded cylindrical portion 9.

Second part 2, also shown in FIG. 1, includes angled body portion 16 having, at its upper end 19, a flat surface that includes an opening with a downwardly-projecting, internally-threaded passage 17. This threaded passage 17 is adapted to receive a threaded, removable, fixation screw joined to a detachable dental prosthesis.

Second part 2 has, at its bottom end, a frustoconical-shaped recess 14 that is complementary in size and shape to frustoconical portion 4 on first part 1. When first part 1 and second part 2 are joined together, frustoconical recess 14 seats sealingly onto frustoconical surface 4 to form a smooth outer profile, as seen in FIG. 2, and to prevent the ingress of solids or liquids into the space between the first and second parts 1 and 2. Projecting downwardly from flat surface 15 is tapered, post means 12 having flat side 13. Post means 12 fits within, and rotates freely in passage 11. Upon cementing of post means 12 in passage 11, however, flat side 13 prevents rotation of post means 12, and, thus, of head means 16 above post means 12.

In use, part 1 is screwed into an internally-threaded passage at the top of a dental implant that has been surgically implanted in the jaw of a patient. Then, post 12 of second part 2 is inserted into passage 11 through hex-hole 8 with sufficient cement placed in passage 11 to insure thorough cementing of post 12 in passage 11. There is sufficient space between the walls of passage 11 and post 12 to permit excess cement to flow upwardly and outwardly from passage 11. Passages 31 and 32 also permit excess cement to flow upwardly and outwardly from passage 11. Post 12 fits sufficiently snugly within passage 11 to minimize or prevent rotation of post 12, and, therefore, of second part 2.

FIG. 2 shows the resulting angled abutment after first part 1 and second part 2 are joined together in the intended way. In the embodiment shown in FIGS. 1 and 2, body portion 16 forms an angle of 30° with respect to the longitudinal axis of post 10.

Figure 4:
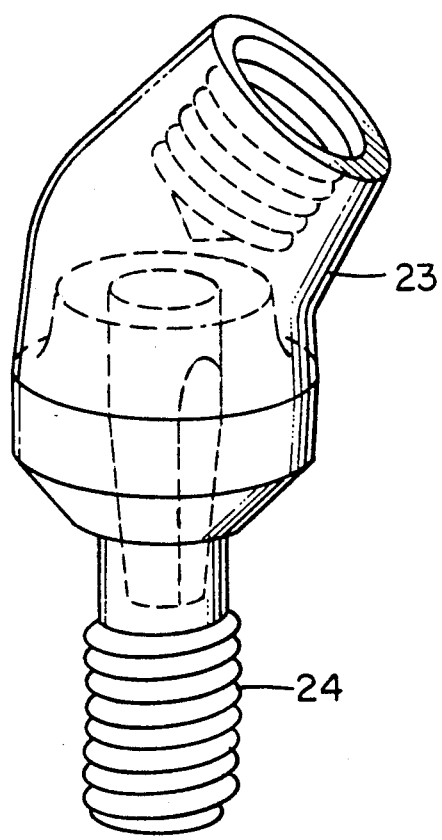
FIG. 4 shows a third embodiment of the angled abutment.
Figure 5A:
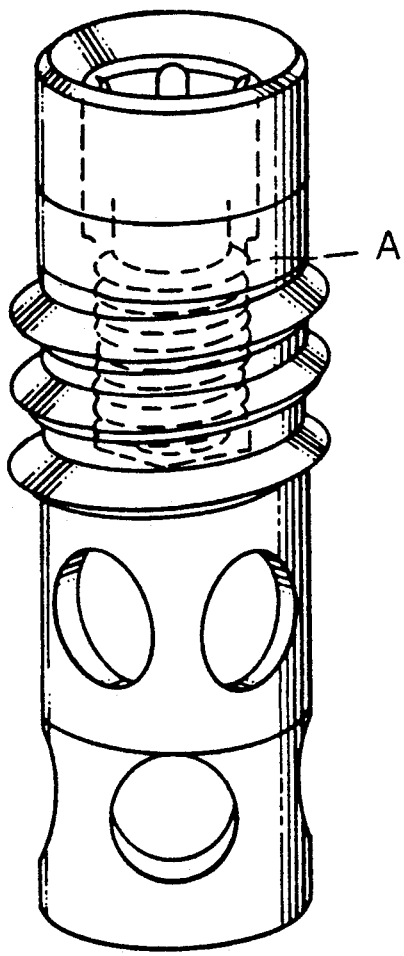
FIGS. 5A and 5B show a Core-Vent ® endosseous dental implant anchoring means with an internally-threaded shaft marked A.
Figure 5B:
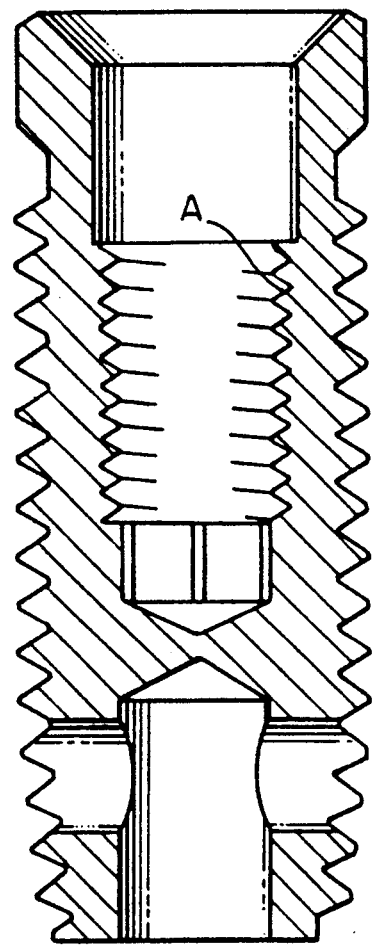
Figure 6A:
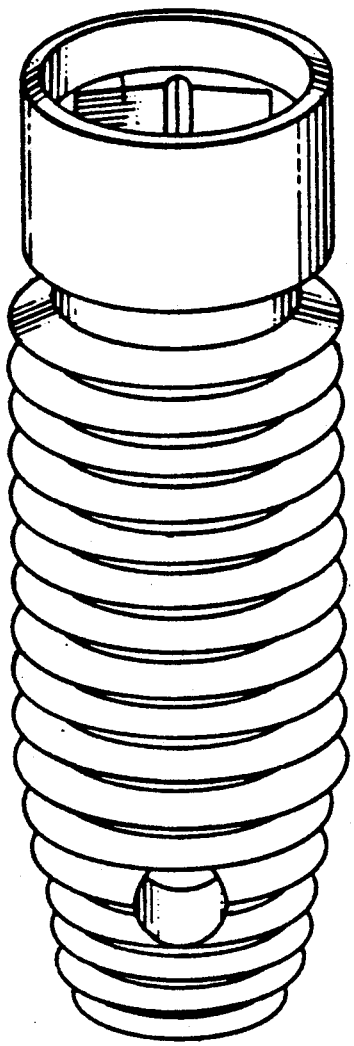
FIGS. 6A and 6B show a Screw-Vent ® endosseous dental implant anchoring means with an internally-threaded shaft marked B.
Figure 6B:
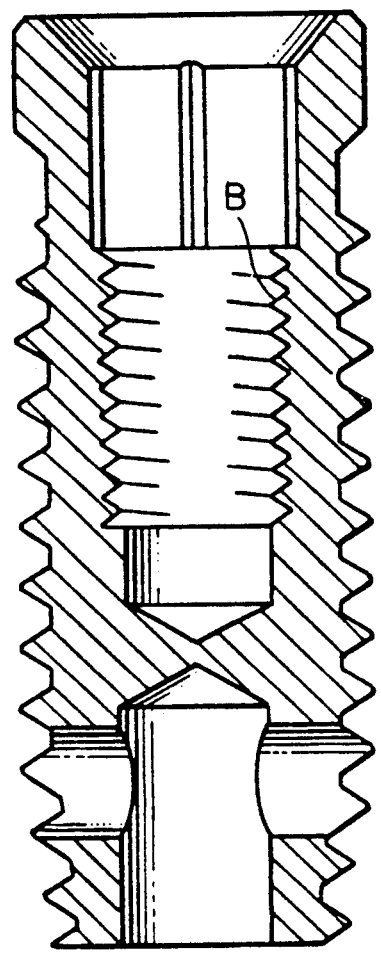
Figure 7A:
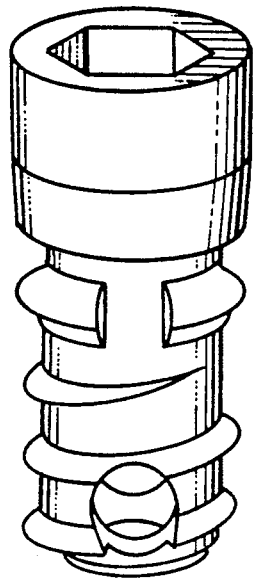
FIG. 7A and 7B show a Micro-Vent ® endosseous dental implant anchoring means with an internally-threaded shaft marked C.
Figure 7B:
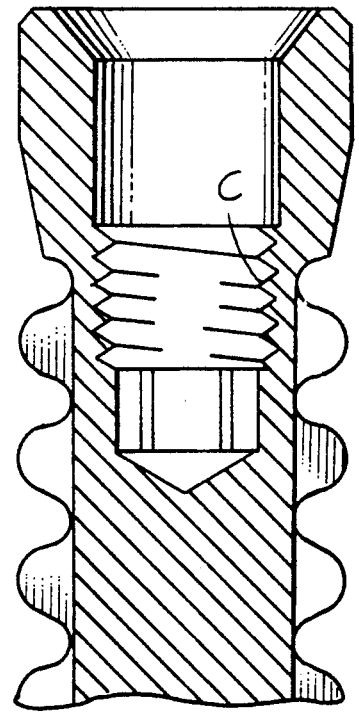
Figure 8A:
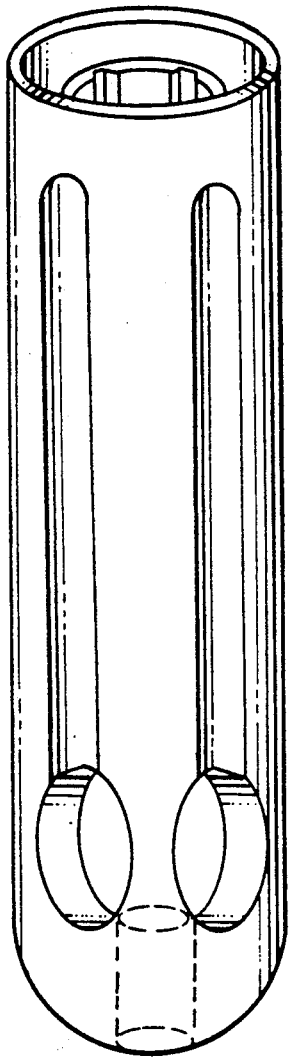
FIGS. 8A and 8B show a Bio-Vent ® endosseous dental implant anchoring means with an internally-threaded shaft marked D.
Figure 8B:
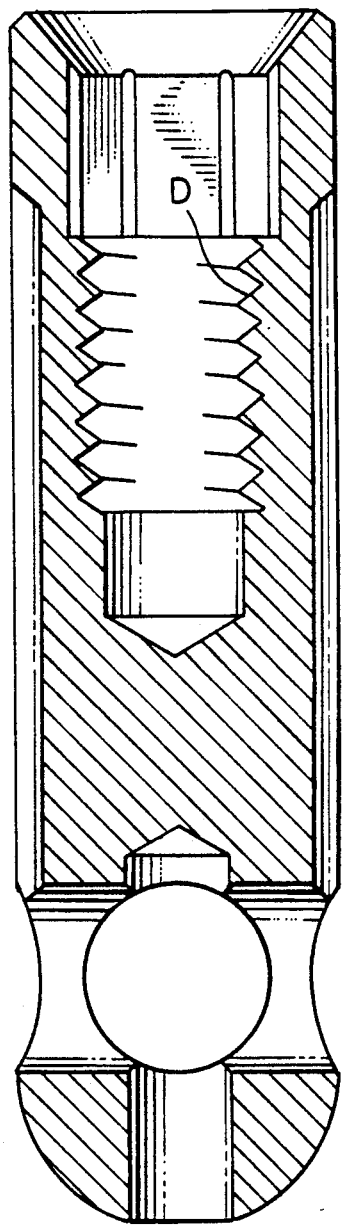

FIGS. 3 and 4 show, respectively, second and third embodiments of the angled abutment depicted in FIGS. 1 and 2. However, in FIG. 3, the second part of the angled abutment has its body portion 20 a 15° angle to the longitudinal axis of post 22. In FIG. 4, head means 23 forms a 40° angle with the longitudinal axis of post 24.

The new angled abutment has several advantages over one-piece, threaded angled abutments. For example, with one-piece, threaded angled abutments, no one could predict the direction the angled head would take once the abutment was firmly seated in the implant. By contrast, the two-part angled abutment of this invention includes a threaded post on the first part to permit detachability of the abutment from the implant while permitting the angled head to be cemented in the first part at any desired position of rotation of the abutment with sufficient strength to resist off-center occlusal forces.

The new angled abutment has several advantages over two-piece, threaded, angled abutments, too. For example, where the first part of the two-part angled abutment was a threaded post with a pillar projecting from the post, and the second part, an angled head to be cemented to the pillar, the angled abutment could not be adapted to receive a fixation screw to retain a detachable prosthesis. Further, an angled head with a threaded opening would necessarily be off-center with a pillar projecting upwardly from the first part. The new two-part angled abutment has neither of these deficiencies.

I claim:

1. An angled abutment adapted for use with an endosseous dental implant anchoring means includes a first part and a second part wherein the first part comprises platform means joined to downwardly-projecting post means having screw threads on the outer surface of said post means, said threaded post means being adapted for engagement in an internally-threaded shaft at the top of an endosseous dental implant, and said second part comprising angled head means joined to shaft means having at least one flat side and projecting downwardly from said angled head means, said angled head means being adapted for insertion and for cementing into a downwardly-projecting passage in said platform means, said passage including a plurality of flat sides.

2. The angled abutment of claim 1 wherein said second part has a tapered shape to accept a cemented dental prosthesis.

3. The angled abutment means of claim 1 wherein said head means has a threaded passage in its upper surface to accept a fixation screw for a detachable dental prosthesis.

4. The angled abutment of claim 1 further comprising means atop said first part, and at the bottom of said second part, that are complementary in size and shape, and that join sealingly when said first part is seated in said second part to substantially prevent inflow of solids and liquids into the space between the first and second parts when they are joined together.

5. The angled abutment of claim 1 wherein the second part forms an angle of approximately 15° with respect to the longitudinal axis of said post means in said first part.

6. The angled abutment of claim 1 wherein the second part forms an angle of approximately 30° with respect to the longitudinal axis of said post means in said first part.

7. The angled abutment of claim 1 wherein the second part forms an angle of approximately 40° with respect to the longitudinal axis of said post means in said first part.

8. A first part of an angled abutment adapted for use with an endosseous dental implant anchoring means comprises platform means joined to downwardly-projecting post means having screw threads on the outer surface of said post means, said platform means including an opening leading to an internal passage, said passage including a plurality of flat sides and being adapted to receive and engage a second part of said angled abutment.

* * * * *